United States Patent
Kakuta

(10) Patent No.: US 11,103,489 B2
(45) Date of Patent: Aug. 31, 2021

(54) DRUG FOR PREVENTING OR TREATING INFLAMMATORY BOWEL DISEASE

(71) Applicant: NATIONAL UNIVERSITY CORPORATION OKAYAMA UNIVERSITY, Okayama (JP)

(72) Inventor: Hiroki Kakuta, Okayama (JP)

(73) Assignee: NATIONAL UNIVERSITY CORPORATION OKAYAMA UNIVERSITY, Okayama (JP)

( * ) Notice: Subject to any disclaimer, the term of this patent is extended or adjusted under 35 U.S.C. 154(b) by 0 days.

(21) Appl. No.: 15/739,815

(22) PCT Filed: Jun. 29, 2016

(86) PCT No.: PCT/JP2016/069319
§ 371 (c)(1),
(2) Date: Dec. 26, 2017

(87) PCT Pub. No.: WO2017/002874
PCT Pub. Date: Jan. 5, 2017

(65) Prior Publication Data
US 2018/0185342 A1  Jul. 5, 2018

(30) Foreign Application Priority Data

Jun. 30, 2015  (JP) .............................. JP2015-132090

(51) Int. Cl.
  *A61K 31/44*  (2006.01)
  *A61P 1/04*  (2006.01)
(52) U.S. Cl.
  CPC ................. *A61K 31/44* (2013.01); *A61P 1/04* (2018.01)
(58) Field of Classification Search
  CPC .............. A61K 2300/00; A61K 31/436; A61K 31/519; A61K 45/06
  See application file for complete search history.

(56) References Cited

U.S. PATENT DOCUMENTS

2010/0120742 A1 * 5/2010 Kakuta .............. A61K 31/4409
                                                          514/211.09
2015/0374632 A1   12/2015 Ryu et al.

FOREIGN PATENT DOCUMENTS

| JP | 2013-177329 A | 9/2013 |
| JP | 2014-076953 A | 5/2014 |
| JP | 2014076953 A * | 5/2014 |
| WO | WO 2008/105386 A1 | 9/2008 |
| WO | 2010/041449 A1 | 4/2010 |
| WO | WO 2010/098125 A1 | 9/2010 |
| WO | WO 2014/129568 A1 | 8/2014 |

OTHER PUBLICATIONS

Desreumaux et al., J Exp Med. Apr. 2, 2001; 193(7): 827-838 (Year: 2001).*
International Search Report (PCT/ISA/210) dated Aug. 9, 2016, by the Japan Patent Office as the International Searching Authority for International Application No. PCT/JP2016/069319.
Written Opinion (PCT/ISA/237) dated Aug. 9, 2016, by the Japan Patent Office as the International Searching Authority for International Application No. PCT/JP2016/069319.
Desreumaux et al., Attenuation of Colon Inflammation through Activators of the Retinoid X Receptor (RXR)/Peroxisome Proliferator-activated Receptor gamma (PPARgamma) Heterodimer: A Basis for New Therapeutic Strategies, *J Exp Med.*, Apr. 2, 2001, pp. 827-838, vol. 193, No. 7, The Rockefeller University Press. http://www.jem.org/cgi/content/full/193/7/827.
Ohsawa et al., Modification at the Lipophilic Domain of RXR Agonists Differentially Influences Activation of RXR Heterodimers, *ACS Medicinal Chemistry.Letters*, Aug. 27, 2010, pp. 521-525, vol. 1, No. 9, American Chemical Society. DOI: 10.1021/ml100184k.
Kakuta et al., Retinoid X Juyotai Partial Agonist Net-4IB no Soshutu to Yakko Fukusayo Hyoka, *Vitamins*, Apr. 2013, p. 254, vol. 87, Medical Online.
Kakuta, Discovery Research of Drugs Targeting Retinoid X Receptors, *Vitamins*, Apr. 2015, pp. 177-178, vol. 89, Medical Online.
Takamatsu et al., The First Potent Subtype-Selective Retinoid X Receptor (RXR) Agonist Possessing a 3-Isopropoxy-4-isopropylphenylamino Moiety, NEt-3IP (RXRα/β-dual agonist), *ChemMedChem*, 2008, pp. 780-787, vol. 3, Wiley-VCH Verlag GmbH&Co. KGaA, Weinheim. DOI: 10.1002/cmdc.200700313.
Furusawa et al.: "RXR partial agonist NEt-4IB exerts therapeutic effects on inflammatory bowel disease without the side effects of RXR full agonists," Division of Medicinal Chemistry Scientific Abstracts for the 248th National Meeting and Exposition, Aug. 13, 2014, American Chemical Society, 248th ACS National Meeting, San Francisco, CA, Aug. 10-14, 2014, abstract (XP-002787151) (2 pages).

(Continued)

*Primary Examiner* — Jean P Cornet
(74) *Attorney, Agent, or Firm* — Buchanan Ingersoll Rooney PC

(57) ABSTRACT

There is provided a drug for preventing or treating inflammatory bowel disease, comprising as an active ingredient an RXR agonist which is a compound represented by Formula (1). In Formula (1), it is preferred that: $R^1$ is an alkyl group; $R^2$ is an alkyl group; W is $NR^3$, and $R^3$ is an alkyl group; $X^1$ is CH; $Y^1$ is N; $X^2$ and $Y^2$ are CH; and Z is a carboxyl group. Thus, a drug capable of strongly preventing or treating inflammatory bowel disease while suppressing the onset of side effects is provided.

(1)

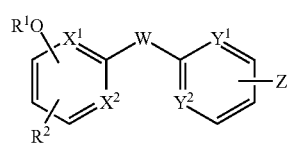

5 Claims, 6 Drawing Sheets

(56) References Cited

OTHER PUBLICATIONS

Knackstedt et al.: "The Importance of the Retinoid X Receptor Alpha in Modulating Inflammatory Signaling in Acute Murine Colitis," Digestive Diseases and Sciences, vol. 59, No. 4, Oct. 22, 2013, pp. 753-759, (14 pages).

Kakuta et al.: "Feasibility of Structural Modification of Retinoid X Receptor Agonists to Separate Blood Glucose-Lowering Action from Adverse Effects: Studies in KKAy Type 2 Diabetes Model Mice," Biological & Pharmaceutical Bulletin (of Japan), vol. 35, No. 4, 1 Jan. 2012, pp. 629-633 (5 pages).

Kakuta et al: "RXR Partial Agonist CBt-PMN Exerts Therapeutic Effects on Type 2 Diabetes without the Side Effects of RXR Full Agonists," ACS Medicinal Chemistry Letters, vol. 3, No. 5, May 10, 2012, pp. 427-432 (6 pages).

Kobayashi et al.: "Positron Emission Tomography to Elucidate Pharmacokinetic Differences of Regioisomeric Retinoid X Receptor Agonists," ACS Medicinal Chemistry Letters, vol. 6, No. 3, Jan. 22, 2015, pp. 334-338 (5 pages).

Extended Search Report issued by the European Patent Office in corresponding European Patent Application No. 16817982.8-1112 dated Feb. 11, 2019 (13 pages).

The First Office Action issued by the State Intellectual Property Office of People's Republic of China in corresponding Chinese Patent Application No. 201680038805.2 dated Jan. 14, 2020 (10 pages including partial English translation).

Claudel et al.: "Reduction of atherosclerosis in apolipoprotein E knockout mice by activation of the retinoid X receptor," Proc Natl Acad Sci (PNAS), U.S.A., Feb. 27, 2001, vol. 98, No. 5, pp. 2610-2615 (6 pages).

Ohsawa et al.: "Modification at the Lipophilic Domain of RXR Agonists Differentially Influences Activation of RXR Heterodimers," American Chemistry Society (ACS), Medical Chemistry Letters, (2010), 1, pp. 521-525 (5 pages).

Jung et al.: "n-3 Fatty acids ameliorate hepatic steatosis and dysfunction after LXR agonist ingestion in mice," Biochimica et Biophysica Acta 1811, (2011), pp. 491-497 (7 pages).

\* cited by examiner

[Fig. 1]
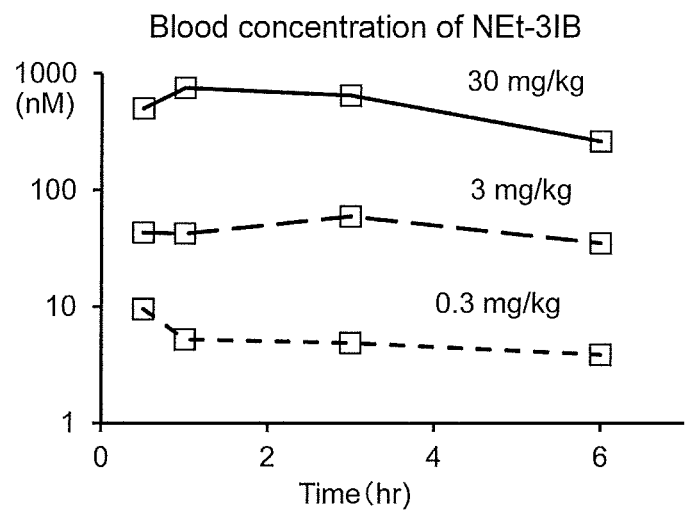
[Fig. 2]
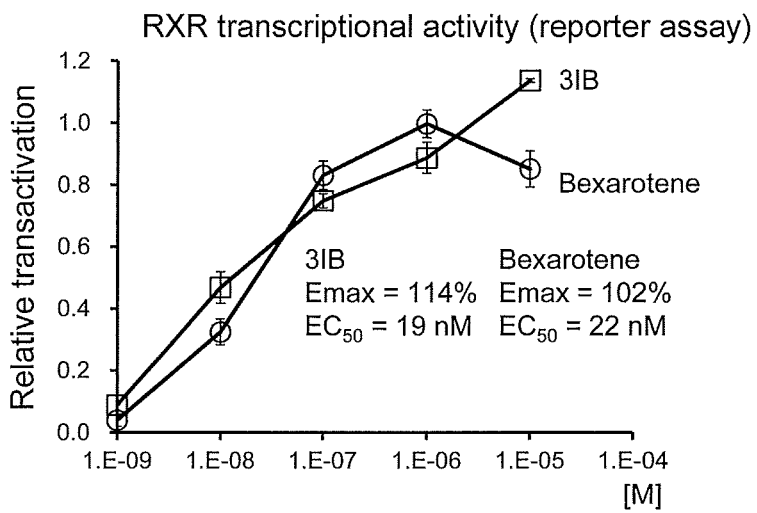

[Fig. 3]
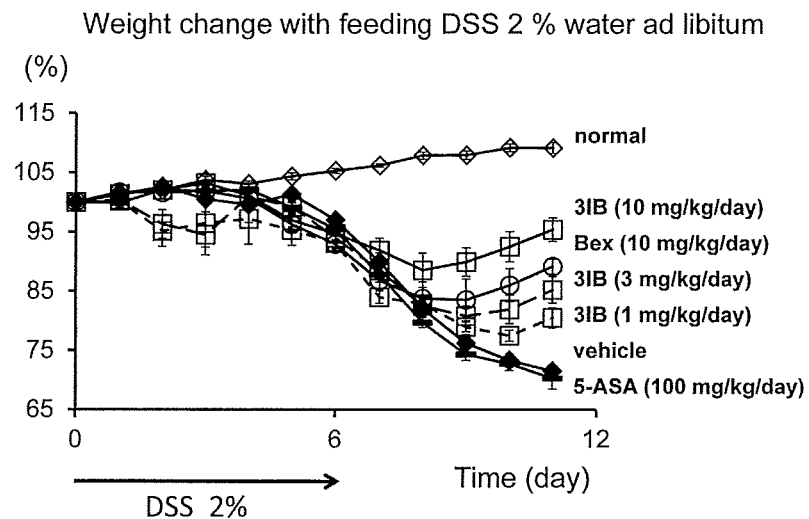
[Fig. 4]
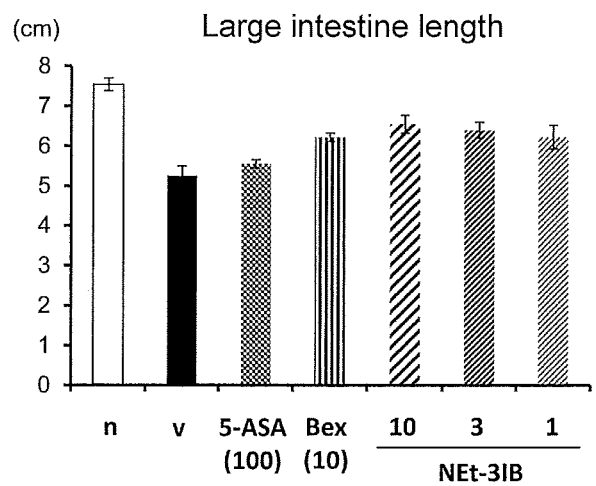

[Fig. 5]
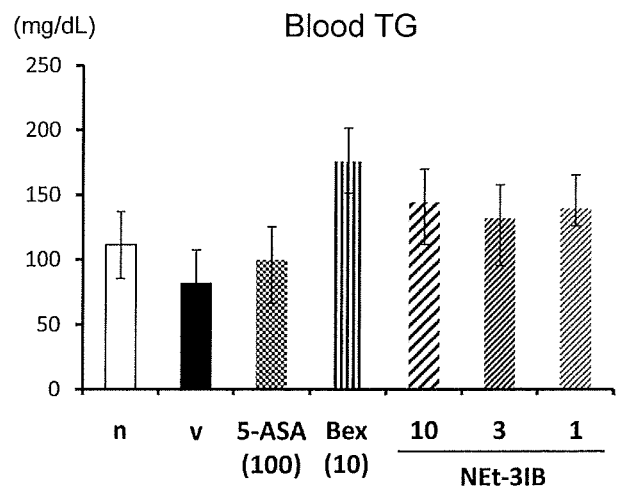
[Fig. 6]
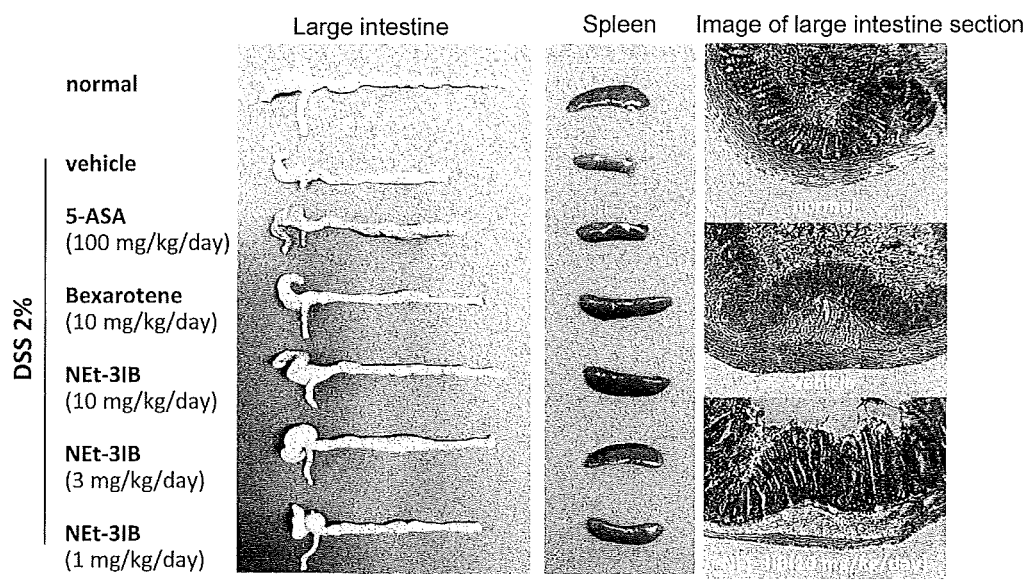

[Fig. 7]
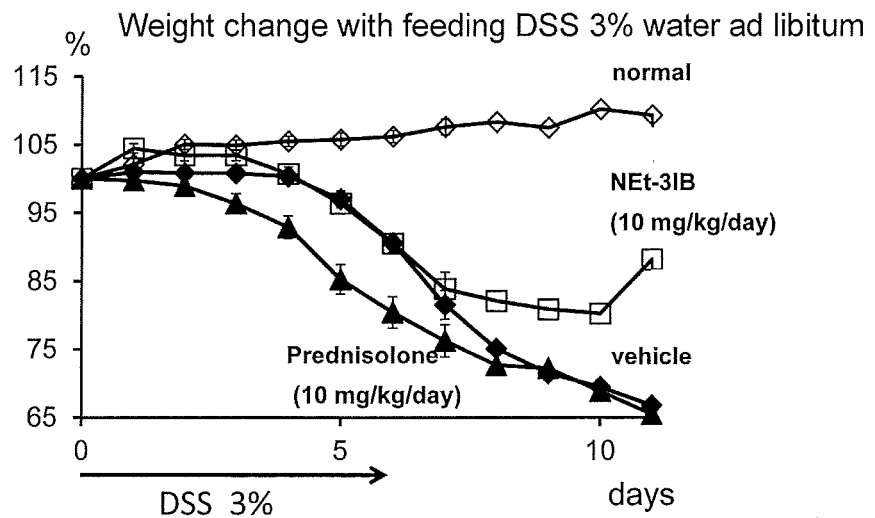
[Fig. 8]
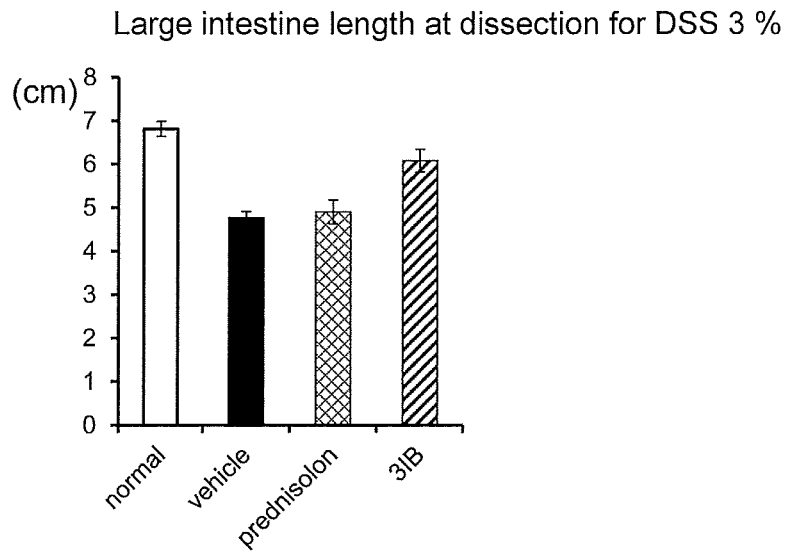

[Fig. 9]
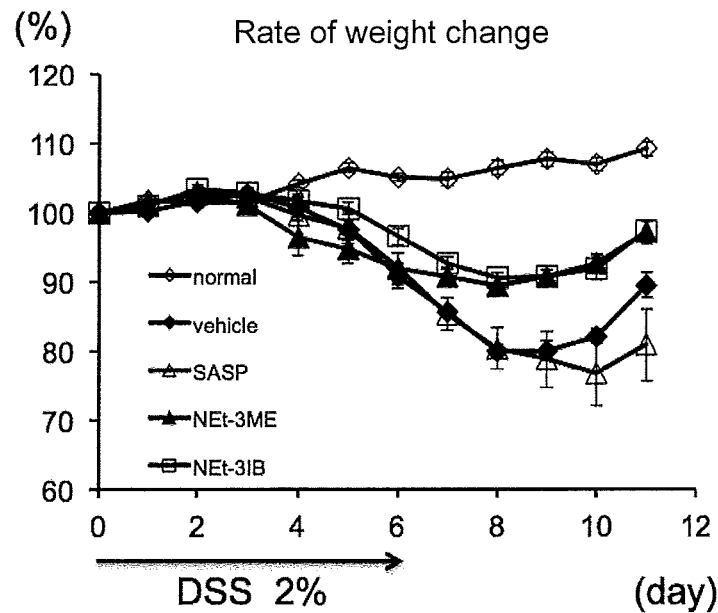
[Fig. 10]
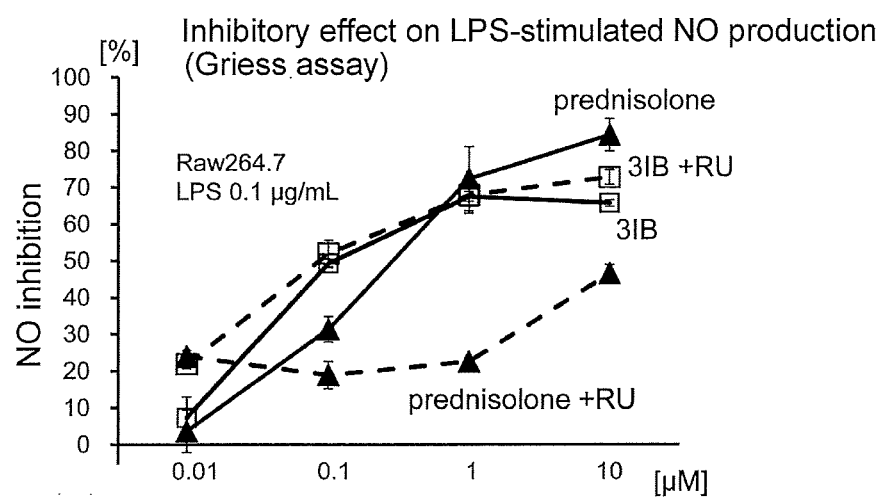

[Fig. 11]
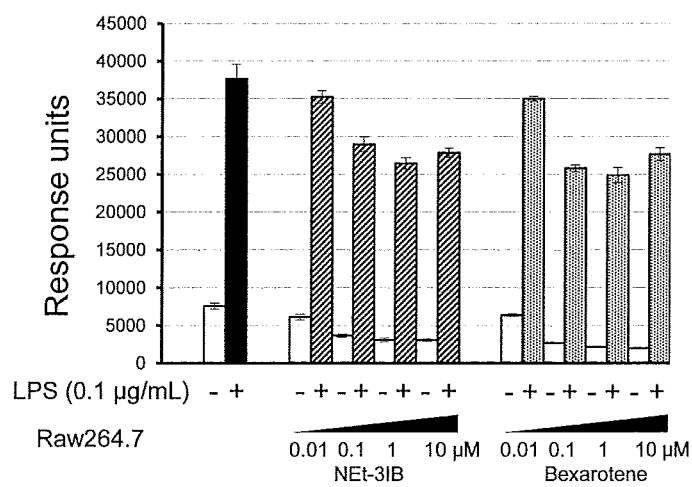

DRUG FOR PREVENTING OR TREATING INFLAMMATORY BOWEL DISEASE

TECHNICAL FIELD

The present invention relates to a drug for preventing or treating inflammatory bowel disease, in particular a drug for preventing or treating inflammatory bowel disease comprising, as an active ingredient, an anti-inflammatory agent which is not or little absorbed by an upper gastrointestinal tract and highly migratory to a lower gastrointestinal tract when being orally administered.

BACKGROUND ART

Inflammatory bowel disease is a collective designation of chronic diseases which cause inflammation of unknown cause in a gastrointestinal tract, and is a refractory disease of unknown cause with long-lasting diarrhea and hematochezia, including ulcerative colitis and Crohn disease. In contrast to general food poisoning, its medical condition is long-lasting and repeatedly relieved and exacerbated.

Therapy of inflammatory bowel disease includes nutrition therapy, medical therapy, surgery treatment and granulocyte apheresis whereby granulocytes recruited to an inflamed site are selectively removed, or the like. In medical therapy, salazosulfapyridine, 5-aminosalicylic acid (mesalazine type formulation), a steroidal anti-inflammatory agent, an immunosuppressant or the like is used. There is, however, a problem of side effects, such as headache and gastritis caused by sulfapyridine as a metabolite for salazosulfapyridine and infection and adrenal cortex insufficiency caused by excessive immunodepressive effect for a steroidal anti-inflammatory agent.

Retinoid X receptor (RXR) forms, independently of a glucocorticoid receptor as a molecular target of a steroidal anti-inflammatory agent, a heterodimer with a peroxisomal proliferator-activated receptor or a liver X receptor which exhibits anti-inflammatory effect and exerts anti-inflammatory effect via activation inhibitory action of an inflammatory/immune-related transcription factor, NF-κB. As its effect, there has been described a therapeutic effect in an inflammatory bowel disease model (Non-patent Reference No. 1). Known RXR full agonists (agonists fully activating RXR) such as RXR agonists described therein have the problem of side effects such as an enlarged liver and increase in a blood triglyceride (TG) value.

Ulcerative colitis, Crohn disease and so on are diseases developed in a lower gastrointestinal tract.

As described above, in order to treat a disease in a lower gastrointestinal tract or prevent exacerbation from ameliorated state in the disease, a drug exhibiting therapeutic effect has to preferentially migrate to a lower gastrointestinal tract. Furthermore, in order to prevent side effects such as an enlarged liver and an increased blood triglyceride value, its migration to a liver or the like has to be inhibited.

For allowing an anti-inflammatory agent to migrate to a lower gastrointestinal tract, the agent is, for example, formulated as an enteric-coated preparation (for example, Patent Reference No. 1).

Non-patent Reference No. 2 has described transcriptional activation potency to RXR by commercially available bexarotene and NEt-3IB, that is, a compound represented by Formula (2) (experimental results from a reporter gene assay).

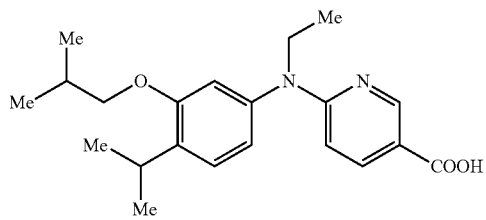

The inventor expected that an agent exhibiting anti-inflammatory effect which is less soluble and less absorbed by an upper gastrointestinal tract consisting of an esophagus, a stomach and a duodenum and thus migrates as it is to a lower gastrointestinal tract would not have to be formulated as a special enteric-coated preparation for allowing for migration to the affected site.

PRIOR ART REFERENCES

Patent References

Patent Reference No. 1: WO 2014/129568A1

Non-Patent References

Non-patent Reference No. 1: J Exp Med. 2001, 193(7), pp 827-838

Non-patent Reference No. 2: ACS Med. Chem. Lett., 2010, 1 (9), pp 521-525

SUMMARY OF THE INVENTION

Problems to be Solved by the Invention

To solve the above problems, an objective of the present invention is to provide a drug which can intensely prevent or treat an inflammatory bowel disease with reduced side effects compared with a conventional method.

Means for Solving the Problems

To solve the above problems, we have intensely investigated and have found an anti-inflammatory agent which is not or little absorbed by an upper gastrointestinal tract and highly migratory to a lower gastrointestinal tract when being orally administered, achieving the present invention.

The above problems can be solved by providing a drug for preventing or treating an inflammatory bowel disease, comprising an RXR agonist as an active ingredient which is a compound represented by formula (1):

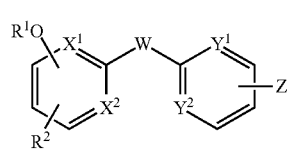

wherein $R^1$ is selected from the group consisting of straight or branched-chain, unsubstituted or substituted alkyl, alkenyl, alkynyl and aryl groups;

$R^2$ is selected from the group consisting of straight or branched-chain, unsubstituted or substituted alkyl, alkenyl, alkynyl, aryl and alkoxy groups;

W is $NR^3$ or $CR^3{}_2$; $R^3$ is selected from the group consisting of hydrogen and straight or branched-chain, unsubstituted or substituted alkyl, alkenyl, alkynyl and aryl groups;

$X^1$ and $Y^1$ are selected from CH and N;

$X^2$ and $Y^2$ are selected from CH, $CR^4$ and N; $R^4$ is selected from straight or branched-chain, unsubstituted or substituted alkyl, alkenyl, alkynyl and alkoxy groups, and a halogen, a nitro group and an amino group;

Z is a carboxyl group bound directly or via a linker selected from the group consisting of alkylene, alkenylene and alkynylene groups.

Here, preferably, $R^1$ is a straight or branched-chain, unsubstituted or substituted alkyl group; $R^2$ is a straight or branched-chain, unsubstituted or substituted alkyl group; W is $NR^3$ and $R^3$ is a straight or branched-chain, unsubstituted or substituted alkyl group; $X^1$ is CH; $Y^1$ is N; $X^2$ and $Y^2$ are CH; and Z is a carboxyl group. More preferably, the compound represented by Formula (1) is represented by Formula (2):

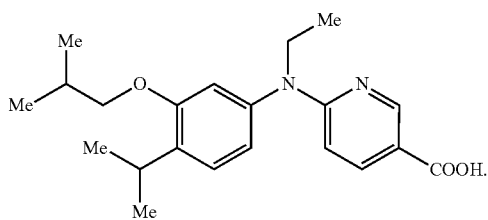

(2)

Preferably, the compound represented by Formula (1) is not or little absorbed by an upper gastrointestinal tract and is highly migratory to a lower gastrointestinal tract. Preferably, the drug of the present invention is orally administered. Further preferably, the drug of the present invention is a drug for preventing or treating ulcerative colitis or Crohn disease.

Effects of the Invention

According to the present invention, poor migration in blood in an upper gastrointestinal tract allows for preventing or treating an inflammatory bowel disease while reducing side effects such as increase in blood triglyceride even with, for example, an RXR agonist (full agonist).

BRIEF DESCRIPTION OF THE DRAWINGS

FIG. 1 shows a blood concentration of NEt-3IB.

FIG. 2 shows activation potency of NEt-3IB to RXR according to a reporter gene assay.

FIG. 3 shows weight change in a DSS (2% aqueous solution) intestinal inflammation model.

FIG. 4 shows a large intestine length in a DSS (2% aqueous solution) intestinal inflammation model.

FIG. 5 shows a blood triglyceride (TG) concentration in a DSS (2% aqueous solution) intestinal inflammation model.

FIG. 6 is photographs of a large intestine and a spleen in a DSS (2% aqueous solution) intestinal inflammation model.

FIG. 7 shows weight change in a DSS (3% aqueous solution) intestinal inflammation model.

FIG. 8 shows a large intestine length in a DSS (3% aqueous solution) intestinal inflammation model.

FIG. 9 shows weight change in a DSS (2% aqueous solution) intestinal inflammation model.

FIG. 10 shows inhibitory effect on LPS-stimulated NO production.

FIG. 11 shows NFκB transcriptional activation inhibitory potency.

MODES FOR CARRYING OUT THE INVENTION

A drug for preventing or treating an inflammatory bowel disease of the present invention is a drug for preventing or treating an inflammatory bowel disease containing as an active ingredient an anti-inflammatory agent which is not or little absorbed from an upper gastrointestinal tract and highly migratory to a lower gastrointestinal tract. The therapeutic drug can be a composition such as a suspension. The anti-inflammatory agent used herein is a compound which is agonistic to a retinoid X receptor (retinoid X receptor; RXR), specifically a compound represented by Formula (1).

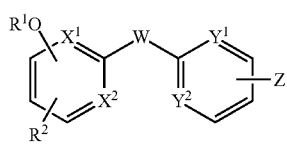

(1)

wherein $R^1$ is selected from the group consisting of straight or branched-chain, unsubstituted or substituted alkyl, alkenyl, alkynyl and aryl groups;

$R^2$ is selected from the group consisting of straight or branched-chain, unsubstituted or substituted alkyl, alkenyl, alkynyl, aryl and alkoxy groups;

W is $NR^3$ or $CR^3{}_2$; $R^3$ is selected from the group consisting of hydrogen and straight or branched-chain, unsubstituted or substituted alkyl, alkenyl, alkynyl and aryl groups;

$X^1$ and $Y^1$ are selected from CH and N;

$X^2$ and $Y^2$ are selected from CH, $CR^4$ and N; $R^4$ is selected from straight or branched-chain, unsubstituted or substituted alkyl, alkenyl, alkynyl and alkoxy groups, and a halogen, a nitro group and an amino group;

Z is a carboxyl group bound directly or via a linker selected from the group consisting of alkylene, alkenylene and alkynylene groups.

In Formula (1), preferably, $R^1$ is a straight or branched-chain, unsubstituted or substituted alkyl group; $R^2$ is a straight or branched-chain, unsubstituted or substituted alkyl group; W is $NR^3$ and $R^3$ is a straight or branched-chain, unsubstituted or substituted alkyl group; $X^1$ is CH; $Y^1$ is N; $X^2$ and $Y^2$ are CH; and Z is a carboxyl group.

More preferably, the compound represented by Formula (1) is represented by Formula (2):

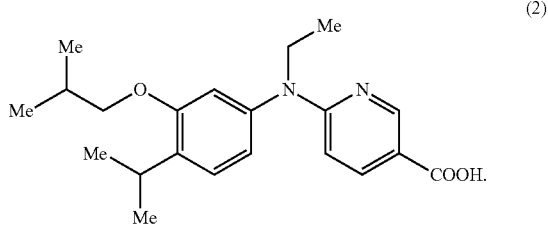 [SMILES: CCN(c1ccc(C(C)C)c(OCC(C)C)c1)c1ccc(C(=O)O)cn1]

(2)

EXAMPLES

There will be specifically described the present invention with reference to Examples, but the present invention is not limited to the range of the examples below.

In this example, two compounds represented by Formulas (2) and (3) were used.

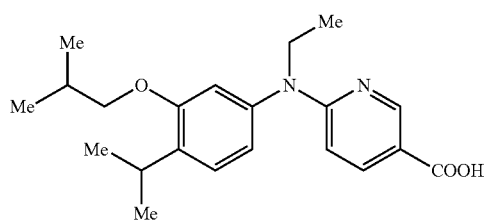

(2)

The compound represented by Formula (2), NEt-3IB, is an RXR full agonist, and reportedly does not cause an enlarged liver or increase in triglyceride in contrast to a conventional RXR full agonist. Furthermore, it has been also reported that it is poorly absorbed in oral administration.

In the light of poor oral absorbability of NEt-3IB, its effect on inflammatory bowel disease was expected to be low. We have, however, surprisingly found that as shown in Examples below, NEt-3IB is highly migratory to a large intestine, and have resultantly demonstrated that in comparison with bexarotene, an existing RXR full agonist, it exhibited prominent anti-inflammatory effect while side effects such as increase in triglyceride can be reduced.

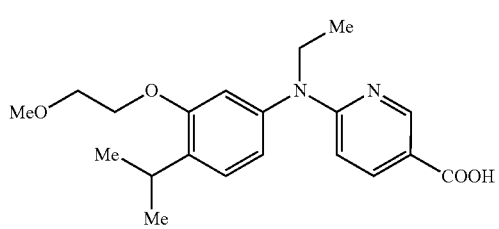

(3)

NEt-3ME, a compound represented by Formula (3), is a RXR agonist with less receptor activation potency than NEt-3IB.

Example 1

Measurement of a Blood Concentration of a Drug

1. Six-week old male ICR mice (body weight: 15 to 25 g) were fasted from the evening of the day before the experiment, and a compound solution prepared in [2] below at a volume of 10 mL/kg was orally administered via a stomach tube. At 0, 1, 3, and 6 hours after the administration, the animals were anesthetized with ether, and incised the abdomen to collect blood from a large vein. The blood was transferred into a heparinized tube and centrifuged at 5000 rpm for 5 minutes, to collect 100 μL of plasma. Each treated group had five mice.

2. A dose of the compound was 30, 3, 0.3 mg/kg per an animal. A dosage form of the compound was prepared by dissolving it in ethanol to a final concentration of 1% and suspending the solution in a 0.5% solution of carboxymethylcellulose (CMC).

3. To 100 μL of the plasma were added 100 μL of an ammonium acetate buffer (prepared by adding acetic acid to 5 mM of ammonium acetate and adjusting a pH to 5), and then 1 mL of ethyl acetate. The mixture was vortexed for 30 min, allowed to stand at room temperature for 10 min and centrifuged for 30 sec to remove 800 μL of a supernatant, which was then concentrated by a centrifugal evaporator. The residue was stored at −20° C.

4. To the sample stored at −20° C. was added 100 μL of methanol, and the mixture was vortexed for 30 sec and centrifuged for 30 sec. Then, for 20 μL of the sample, a compound concentration was determined by HPLC or LCMS.

The results obtained are shown in FIG. 1. In a single dose of 3 mg/kg, a blood concentration of NEt-3IB did not reach 100 nM at any administration time, and FIG. 2 shows that RXR was activated only to the extent of 50%. FIG. 2 was cited from Non-patent Reference No. 2.

Example 2

Measurement of a Drug Concentration in Feces

1. For each treated group, four six-week old male ICR mice (body weight: 35 to 40 g) were used.

2. An orally-administered solution was prepared by dissolving it in ethanol to a final concentration of 1% and suspending the solution in a 0.5% solution of carboxymethylcellulose (CMC).

3. Each mouse was housed in a cage and had free access to feed and water.

4. After a body weight was measured at 10 a.m., the animal was gavaged with an evaluated drug via a feeding tube.

5. From the next day, feces in each cage were collected for 3 days.

6. Hundred milligrams of the feces were dried under vacuum at 40° C. and pulverized in a mortar. Then, 1.5 mL of HPLC-grade methanol was added, followed by ultrasonic extraction for 20 min.

7. After the extraction, the mixture was centrifuged at 4° C. and 1,500×g for 20 min.

8. After the centrifugation, 1 mL of the supernatant was filtered through a syringe filter and poured into a 2 mL Eppendorf tube.

9. A concentration of NEt-3IB in the methanol extract was determined by LC/MS (API4000™). The concentration was converted to a concentration per 100 mg of feces.

10. Since extraction with 1.5 mL of methanol was conducted assuming that 100 mg of the above feces corresponded to 100 μL, a concentration in feces was estimated by multiplying the concentration in methanol determined by LC/MS by 16.

Example 3

Measurement of a Drug Concentration in a Large Intestine

1. The next day of the last medication (day 3 of medication), a mouse used in Example 2 was euthanized with ether and then a large intestine was excised.

2. Faces were removed from the removed large intestine and the inside of the large intestine was washed with PBS. Excess water was removed with Kimwipes.

3. About 200 mg of the above large intestine was precisely placed in a 2 mL Eppendorf tube.

4. To the Eppendorf tube was added 800 μL of HPLC-grade methanol, and the mixture was pulverized by a homogenizer. Methanol was further added such that the total volume of methanol added became five times as much as the volume of the large intestine.

5. The mixture was ultrasonic-extracted for 20 min.

6. After the extraction, the extract was centrifuged at 4° C. and 1,500×g for 20 min.

7. After the centrifugation, about 1 mL of the supernatant was filtered through a syringe filter and poured into a 2 mL Eppendorf tube.

8. A concentration of NEt-3IB in the methanol extract was determined by LC/MS (API4000™).

9. Since extraction with 800 mL of methanol was conducted assuming that 200 mg of the above feces corresponded to 200 μL, a concentration in a large intestine was estimated by multiplying the concentration in methanol determined by LC/MS by 5.

NEt-3IB concentrations in the feces obtained in Example 2 were 40±6 μM, 33±4 μM, and 22±1 μM at Days 1, 2 and 3, respectively. An NEt-3IB concentration in a large intestine obtained in Example 3 the next day after 3 day administration was 2.7±0.3 nM. As demonstrated by these results, the prominent presence of NEt-3IB in feces is found, and increase in the concentration by repeated administration was not found.

Example 4

Preparation of DSS Colitis Model Mice and Evaluation of Drug Efficacy and Side Effects (1)

1. Six-week old (body weight: 20 g) male C57BL/6 mice were purchased and acclimated for 5 to 7 days.

2. An average weight was mated between groups having 5 to 6 animals.

3. A DSS untreated group (normal) had free access to mineral water filtered through a 0.22 μM membrane filter. A DSS untreated group (vehicle and drug group) had free access to mineral water containing 2% dextran sulfate sodium (DSS) filtered through a 0.22 μM membrane filter for 6 days and then mineral water filtered through a 0.22 μM membrane filter.

4. After initiation of free access to DSS-containing water, a body weight was measured every day and then an evaluated drug was orally administered.

5. Evaluated drug administered were 5-aminosalicylic acid (5-ASA; 100 mg/kg/day), bexarotene as an RXR full agonist (10 mg/kg/day), NEt-3IB as an RXR full agonist at 10 mg/kg/day, 3 mg/kg/day, 1 mg/kg/day.

6. An orally administered solution was prepared by dissolving the drug in ethanol to a final concentration of 1% and suspending the solution in a 0.5% solution of carboxymethylcellulose (CMC).

7. The drug was administered for 11 days, and the next day, a mouse was euthanized followed by blood collection and dissection. A large intestine and a spleen were isolated. A large intestine length was measured and photographs of the large intestine and the spleen were taken. A section of the large intestine was taken and photographed.

8. The collected blood was heparinized to give plasma, which was used for determining a blood triglyceride (TG).

FIG. 3 shows weight change in mice. FIG. 4 shows a large intestine length. FIG. 5 shows a blood TG concentration. FIG. 6 shows photos of a large intestine and a spleen, and images of a large intestine section. 5-Aminosalicylic acid, even at a dose of 100 mg/kg/day, did not contribute to improvement in body weight reduction and recovery of a large intestine length. NEt-3IB administered in repeated oral dosing at 10 mg/kg/day exhibited, in comparison with bexarotene, prominent improvement in body weight reduction and recovery of a large intestine length. In contrast to bexarotene, NEt-3IB inhibited increase in blood TG.

Example 5

Preparation of DSS Colitis Model Mice and Evaluation of Drug Efficacy and Side Effects (2)

A test was conducted as described in Example 4, except that a DSS concentration was 3% and in addition to NEt-3IB (10 mg/kg/day), a steroidal anti-inflammatory agent, prednisolone (10 mg/kg/day) as a control agent was administered.

FIG. 7 shows weight change in mice, and FIG. 8 shows a large intestine length. Prednisolone did not exhibit anti-inflammatory effect by oral administration at 10 mg/kg/day, while NEt-3IB exhibited prominent inhibition of body weight reduction and recovery of a large intestine length.

Example 6

Preparation of DSS Colitis Model Mice and Evaluation of Drug Efficacy and Side Effects (3)

A test was conducted as described in Example 4, except that in addition to NEt-3IB (10 mg/kg/day), NEt-3ME (30 mg/kg/day) and salazosulfapyridine (SASP) (200 mg×2/kg/day) as a control anti-inflammatory agent were administered.

FIG. 9 shows weight change in mice. It is indicated that an existing drug for inflammatory bowel disease, SASP, did not exhibit improvement effect compared with a vehicle, while both NEt-3IB and NEt-3ME inhibited body weight reduction and suppressed enteritis. NEt-3ME exhibited effect comparable to NEt-3IB at a dose three times as much as NEt-3IB.

Example 7

Inhibitory Effect on LPS-Stimulated NO Production (Griess Assay)

(Day 1): On a 96-well plate, Raw264.7 cells were inoculated at $1.0 \times 10^5$ cells/well.

(Day 2): LPS (lipopolysaccharide) (100 ng/mL) and each RXR in DMSO (final concentration: 0.1%) were added and the plate was incubated for 48 hours.

(Day 4): For 50 μL of the culture supernatant, an NO (nitrogen monoxide) concentration was determined by Griess method (employing PROMEGA G2930).

The results are shown in FIG. 10. RU in the figure means that prednisolone was combined with 1 μM of RU486, an antagonist of a glucocorticoid receptor (GR) which is a target molecule of prednisolone. NO production by stimulating Raw264.7 cells with LPS was also inhibited by prednisolone or NEt-3IB as an RXR agonist. NO-production inhibitory effect by prednisolone was inhibited by combination use of RU486 as a GR antagonist, while such effect by NEt-3IB was not inhibited. This indicates that molecular target of NO-production inhibitory effect by NEt-3IB was not GR. Thus, it indicates that GR-mediated side effects such as infection induction, moon face and diabetes can be prevented.

Example 8

NFκB Transcriptional Activity Inhibition (Reporter Assay)

Using recombinant RAW264.7 cells in which a secreted alkaline phosphatase (SEAP) gene was incorporated downstream of a transcriptional responsive sequence of NFκB, inhibition effect of NEt-3IB and bexarotene as an RXR agonist on NFκB transcription was investigated. In the experiment, NFκB/SEAPorter RAW Cell Line commercially available from Novus biologicals, LLC was used.

(Day 1): On a 96-well plate, RAW (NF-κB-SEAP) cells were inoculated at $5\times10^5$ cells/well, and were cultured at 37° C. under 5% $CO_2$.

(Day 2): LPS (100 ng/mL) and a test compound were added and culturing at 37° C. under 5% $CO_2$ was continued. Here, LPS was stocked as a PBS solution and the test compound was stocked as a DMSO solution, and they were added such that a final concentration in PBS or DMSO was 0.5%.

(Day 3):

1. Twenty-four hours after addition of LPS and the test compound, 25 μL of the culture supernatant was dispensed to a 96-well white plate and use for determining SEAP activity. Here, a supernatant was also taken from the well containing only the medium (no cells were inoculated) for being used as a background. Furthermore, MTT assay was conducted for the cells remaining in the transparent plate, and SEAP activity was adjusted for a cell count.

2. To the dispensed culture supernatant was added a 1× dilution buffer at 25 μL/well. The wells were covered by a tape and incubated in an oven set to 65° C. for 30 min.

3. The plate was removed from the oven and incubated at 4° C. for 15 min.

4. After removing the tape, a substrate solution was added at 10 μL/well, and the mixture was stirred and incubated under light shielding at room temperature for 60 min.

5. Fluorescence at Ex/Em=360/465 nm was measured by a fluorescence plate reader.

The results are shown in FIG. 11. As a result, it is shown that any RXR agonist at 0.1 μM or more inhibits NFκB transcriptional activity although it is incomplete.

All of the animal experiments were performed under the approval of the Animal Care and Use Committee, Okayama University.

As detailed above, NEt-3IB migrated to feces and exhibited prominent anti-inflammatory effect on DSS enteritis even with a blood concentration of 1 mg/kg/day which is below EC50 to RXR in repetitive oral administration. Furthermore, increase in a blood triglyceride by the agent was reduced, compared with an existing RXR agonist such as bexarotene and prednisolone. Thus, the agent can be used as such a medicine because it is expected to be an active ingredient for preventing or treating an inflammatory bowel disease.

The invention claimed is:

1. A method for treating an inflammatory bowel disease, comprising administering a therapeutically effective amount of a drug comprising an RXR agonist as an active ingredient which is a compound represented by Formula (2):

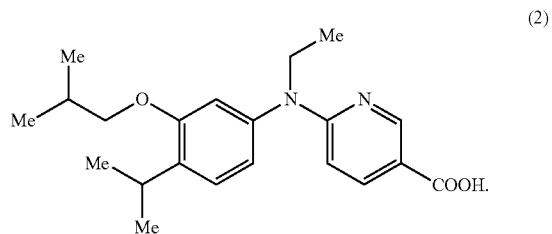 [SMILES: CCN(c1ccc(C(C)C)c(OCC(C)C)c1)c1ccc(C(=O)O)cn1]

2. The method for treating an inflammatory bowel disease as claimed in claim 1, wherein the compound represented by Formula (2) is not or little absorbed by an upper gastrointestinal tract and is highly migratory to a lower gastrointestinal tract.

3. The method for treating an inflammatory bowel disease as claimed in claim 1, wherein the drug is orally administered.

4. The method for treating an inflammatory bowel disease as claimed in claim 1, wherein the inflammatory bowel disease is ulcerative colitis or Crohn disease.

5. The method for treating an inflammatory bowel disease as claimed in claim 1, wherein the therapeutic amount is from 0.3 mg/kg to 30 mg/kg of a patient.

* * * * *